(12) United States Patent
Chang et al.

(10) Patent No.: US 6,676,636 B2
(45) Date of Patent: *Jan. 13, 2004

(54) SOLID BLUNT FOR A NEEDLE ASSEMBLY

(75) Inventors: Joseph Jawshin Chang, Irving, TX (US); Philip D. Schmidt, Arlington, TX (US); Dennis M. Bialecki, Oxford, CT (US)

(73) Assignee: Medex, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/098,646

(22) Filed: Mar. 13, 2002

(65) Prior Publication Data

US 2002/0147428 A1 Oct. 10, 2002

Related U.S. Application Data

(63) Continuation of application No. 09/221,272, filed on Dec. 23, 1998, now Pat. No. 6,391,007.

(51) Int. Cl.$^7$ .............................................. A61M 5/178
(52) U.S. Cl. ......................... 604/164.02; 604/170.02; 604/272
(58) Field of Search ................................ 604/160, 164, 604/165, 166, 170, 168, 263, 264, 272–274, 165.04, 164.01, 170.01, 164.02, 166.01, 170.02, 168.01, 165.01, 165.02, 165.03

(56) References Cited

U.S. PATENT DOCUMENTS

| | | |
|---|---|---|
| 3,788,320 A | 1/1974 | Dye |
| 4,610,671 A | 9/1986 | Luther |
| 4,619,643 A | 10/1986 | Bai |
| 4,828,547 A * | 5/1989 | Sahi et al. ................... 604/110 |
| 5,009,642 A | 4/1991 | Sahi |
| 5,201,712 A | 4/1993 | Bryant |
| 5,472,430 A | 12/1995 | Vaillancourt |
| 5,490,521 A | 2/1996 | Davis et al. |
| 5,540,662 A | 7/1996 | Nicholson |
| 5,743,882 A | 4/1998 | Luther |
| 6,391,007 B2 * | 5/2002 | Chang et al. .......... 604/164.01 |
| 6,520,938 B1 | 2/2003 | Funderburk et al. |
| 6,544,239 B2 | 4/2003 | Kinsey et al. |

FOREIGN PATENT DOCUMENTS

| | | |
|---|---|---|
| EP | 0 657 184 A1 | 6/1995 |
| WO | WO 97/39786 | 10/1997 |

* cited by examiner

Primary Examiner—Manuel Mendez
Assistant Examiner—Jennifer Maynard
(74) Attorney, Agent, or Firm—Wood, Herron & Evans, LLP (57) ABSTRACT

A solid blunt and a needle assembly having a solid blunt. The solid blunt helps to prevent accidental needle sticks. In one exemplary embodiment, a solid blunt has an outer dimension (e.g. outer diameter) which is nearly equal to an inner dimension (e.g. inner diameter) of a cannula of a needle which is configured to contain the solid blunt. In one example, the solid blunt substantially blocks fluid flow in a first circumferential portion of an inner diameter of the cannula and allows fluid flow in a second circumferential portion of the inner diameter. The solid blunt is typically capable of longitudinal movement through the cannula and is prevented from moving substantially in a direction perpendicular to the longitudinal movement. A needle assembly, in another exemplary embodiment, includes a solid blunt, a cannula and a clip which couples slidably the solid blunt to a frame which is coupled to the cannula. The present invention may be used with medical devices including needles, introducers and catheters and other devices as well.

9 Claims, 5 Drawing Sheets

SOLID BLUNT FOR A NEEDLE ASSEMBLY

This is a continuation of Ser. No. 09/221,272, filed on Dec. 23, 1998, now U.S. Pat. No. 6,391,007 entitled, SOLID BLUNT FOR A NEEDLE ASSEMBLY.

BACKGROUND FOR THE INVENTION

1. Field of the Invention

The present invention relates to medical devices and other similar devices and in particular to medical devices such as intravenous catheters and syringes which include a hollow needle having a sharp distal end for piercing an object, such as the skin of a patient.

2. Background of the Invention

The existence of infectious diseases has highlighted the danger to which medical personnel may be exposed when treating patients by means of catheter devices and syringes where a sharp needle point is used to pierce the skin of the patient. In order to protect medical personnel against inadvertent needle stick, a number of solutions have been developed whereby a protective mechanism, incorporated within a catheter or syringe, prevents physical contact with the sharp needle point after use and hence protects against inadvertent needle stick. Many of the developed solutions are complicated. For example, some developments utilize the retraction of the needle within a housing once the needle has been used. Other developments utilize blunts which are contained within the cannula of the hollow needle.

These blunts come in two principal forms: hollow blunts which are hollow tubes concentrically disposed within the circular shaft of a hollow needle, and solid blunts. Hollow blunt designs require that an exit hole be provided at a proximal location to allow blood to exit the blunt and enter a flash chamber, the use of which is well known in the art. In order for blood flashback to be seen as quickly as possible, the exit hole needs to be located just proximal to the butt end of the needle. Thus, hollow blunts require extra machining or manufacturing steps in order to produce a satisfactory hollow blunt. Solid rod blunts are typically cylindrical rods which have an outer diameter which is sufficiently smaller than the inner diameter of the shaft of the cannula of the needle in order to allow clearance for fluid flow all around the diameter of the solid rod blunt. While some prior art designs have included grooves in the solid rod blunt, these solid rod blunts nevertheless position the wall of the blunt (the outside diameter of the blunt) some distance from the inner diameter of the shaft of the cannula.

Figure 1A:
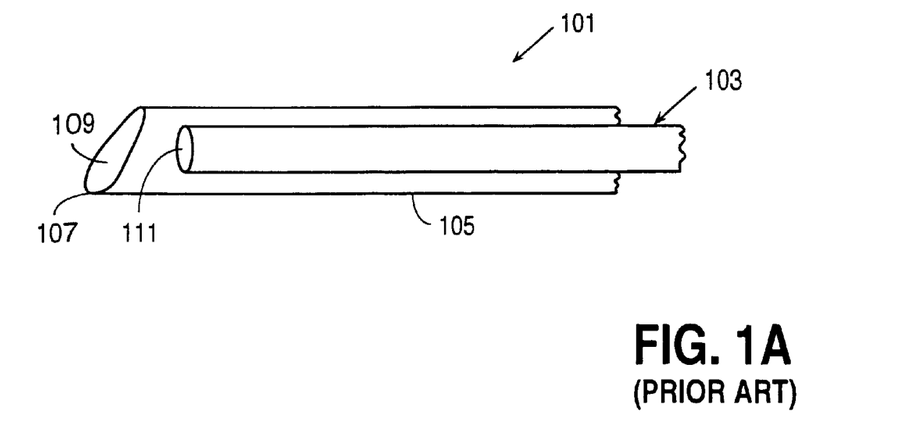
FIG. 1A shows a cross-sectional view of a prior art blunt within a needle shaft. This view depicts the typical position of the blunt relative to the shaft and tip of the needle before use of the needle.
Figure 1B:
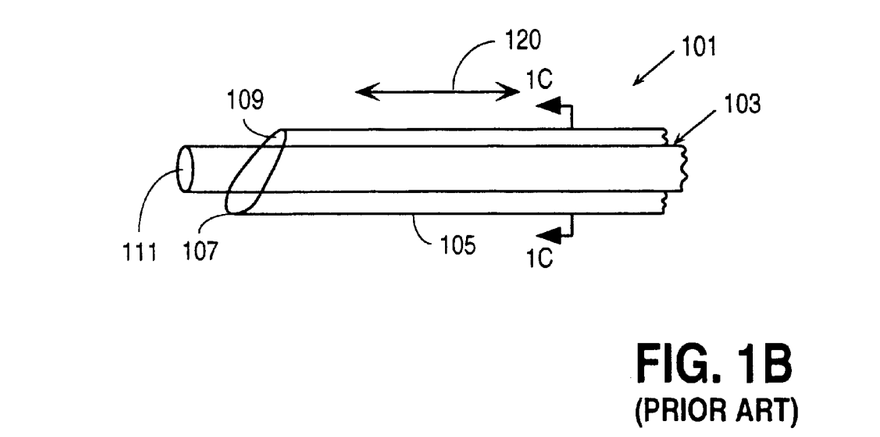
FIG. 1B shows a cross-sectional view of a prior art needle assembly having a blunt which is extended beyond the tip of the needle after use of the needle.
Figure 1C:
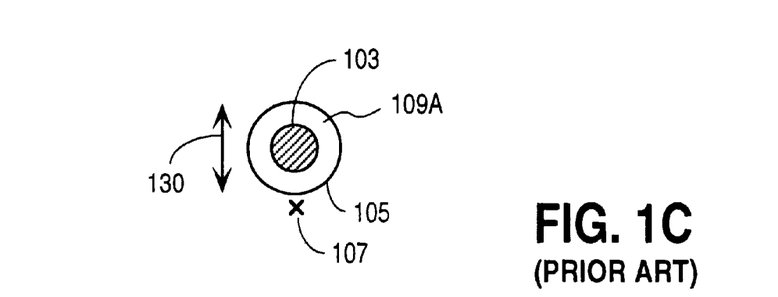
FIG. 1C shows a cross-sectional view of a solid blunt within a needle shaft; this cross-sectional view is taken along the line 1C—1C shown in FIG. 1B.

FIG. 1A illustrates an example of a prior art solid blunt 103 within the shaft 105 of the needle assembly 101. The needle 107 includes a hollow opening 109 and a sharp tip 107 at the end of the opening. The needle assembly 101 is shown in FIG. 1A before its use. In this situation, the solid rod blunt 103 is disposed entirely within the shaft of the needle 105 such that the sharp point 107 can pierce an object, such as the skin of a patient. After use, the solid rod blunt 103 is advanced longitudinally along the longitudinal axis 120 shown in FIG. 1B such that the end 111 of the solid blunt 103 extends beyond the opening of the shaft 105, thereby to some extent covering the sharp tip 107 so that a user of the needle may not receive an accidental needle stick. As is well known in the art, a clip or other mechanism holds the solid blunt rod 103 relative to the shaft 105, preventing it from moving longitudinally along the axis 120 once the blunt 103 has been extended beyond the opening. However, as shown in FIG. 1C, it is also possible for the solid blunt 103 to move perpendicularly to the longitudinal axis 120 and this tends to increase the gap between the blunt and the sharp tip which tends to increase the likelihood of an accidental needle stick or skive. FIG. 1C shows a cross-sectional view of the assembly 101 shown in FIG. 1B at the line 1C—1C shown in FIG. 1B. As can be seen from FIG. 1C, there is a considerable gap 109a between the inner diameter of the shaft 105 and the outer diameter of the solid blunt rod 103. This makes it possible for the rod to move up and down along the axis 130 which is perpendicular to the longitudinal axis 120 shown in FIG. 1B. As a result, it is possible for the blunt 103 to be pushed away from the sharp tip 107 even when it is extended out beyond the tip 107 as shown in FIG. 1B. As a result, even though the blunt may be advanced longitudinally beyond the end of the sharp tip of the needle, the gap between the wall of the blunt and the sharp tip may be so large that the sharp point is permitted to scratch or skive a person's skin. Naturally, the solid blunt must provide space around its circumference in order to permit fluid flow, and thus it would appear that a gap 109a is required.

From the above discussion, it can be seen that it is desirable to provide an improved solid blunt which better protects a user of a needle.

SUMMARY OF THE INVENTION

The present invention provides a solid blunt which helps to prevent accidental needle sticks. The present invention also provides a needle assembly having a solid blunt.

In one exemplary embodiment, a solid blunt has an outer dimension (e.g. outer diameter) which is nearly equal to an inner dimension (e.g. inner diameter) of a cannula of a needle which is configured to contain the solid blunt.

In one example, the solid blunt substantially blocks fluid flow along a first circumferential portion of an inner diameter of the cannula and allows fluid flow in a second circumferential portion of the inner diameter. The solid blunt is typically capable of longitudinal movement through the cannula and is prevented from moving substantially in a direction perpendicular to the longitudinal movement.

A needle assembly, in another exemplary embodiment, includes a solid blunt, a cannula, and a clip which couples the solid blunt to a frame which is coupled to the cannula. The clip allows the solid blunt to move longitudinally between at least two positions and the clip prevents the solid blunt from rotating within the shaft of the needle. The solid blunt itself is effectively lodged within the shaft of the needle so that it cannot move substantially in a direction perpendicular to the longitudinal movement of the solid blunt.

The present invention may be used with medical devices, including needles, catheter assemblies and introducers for catheters and other devices as well.

BRIEF DESCRIPTION OF THE DRAWINGS

The present invention is illustrated by way of example and not limitation in the figures of the accompanying drawings in which like references indicate similar elements.

FIGS. 3A, 3B, 3C, and 3D show cross-sectional views of the blunts shown respectively in FIGS. 2A, 2B, 2C, and 2D within the shaft of a needle. FIGS. 3A, 3B, 3C, and 3D also illustrate the relative position of portions of the blunt and the sharp tip 311 of the needle and blunt assembly.

DETAILED DESCRIPTION

The present invention provides various examples of solid blunts and needle assemblies containing solid blunts. The following description and drawings are illustrative of the invention and are not to be construed as limiting the invention. Numerous specific details are described to provide a thorough understanding of the invention. For example, very specific geometries and dimensions are provided for purposes of illustrating the invention. In certain instances, well known or conventional details are not described in order to not unnecessarily obscure the present invention in detail.

Generally, a solid blunt according to the present invention has an outer dimension, such as an outer diameter, which is nearly equal to (e.g. just less than) an inner dimension, such as an inner diameter, of a cannula of a needle which is configured to contain the solid blunt. At least a portion of the solid blunt having this outer dimension is configured to be positioned near a sharp tip of the needle when the blunt is positioned to protect against needle skiving, such as when the blunt is extended longitudinally out beyond the opening of the needle. The solid blunt is formed in a manner to provide a fluid flow through a fluid path of sufficient size while positioning the surface of the blunt (e.g. the outside diameter) as close to the sharp point of the needle (e.g. inside diameter) as possible. Thus, at least a portion of the solid blunt may substantially block fluid flow along a first circumferential portion of an inner diameter of the cannula while allowing fluid flow in a second circumferential portion of the inner diameter. A typical blunt according to the present invention may be capable of longitudinal movement through the cannula but be prevented from moving substantially in a direction which is perpendicular to the longitudinal movement. By being prevented from moving in this perpendicular direction, the outside dimension of the blunt will be positioned close to the sharp point of the needle and thereby reduce the likelihood that the sharp point will scratch or skive a person's skin.

Figure 2A:
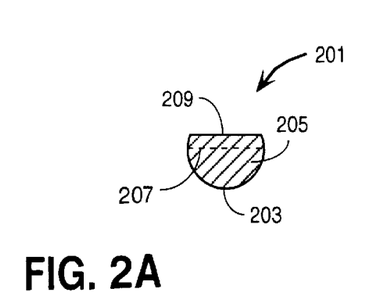
FIGS. 2A, 2B, 2C, and 2D show cross-sectional views of four examples of solid blunts according to the present invention.

FIG. 2A shows an example of a solid blunt 201 which has one particular geometry which resembles the letter "D" in the cross-sectional view of the solid blunt 201. This solid blunt 201 includes an outer circumferential portion or surface 203 and an upper flat portion 209. The solid interior 205 of the blunt extends from the circumferential portion 203 beyond the centerline 207 and up to the flat portion 209. The centerline 207 is designed to be the central diameter of a cannula which receives the solid blunt 201.

Figure 3A:
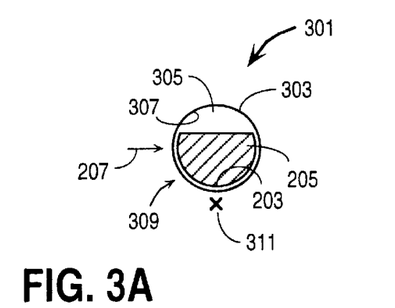

FIG. 3A shows an example of a needle assembly 301 which includes the solid blunt 201 and the shaft 303 of a needle. The solid blunt is disposed within the shaft of the needle 303 such that the bulk of the solid blunt is positioned near the needle's sharp tip 311 which is shown diagrammatically in the cross-sectional view of FIG. 3A. As can be seen from FIG. 3A, the circumferential portion 203 of the outer surface of the solid blunt is closely positioned to the inner diameter 307 of the shaft 303. Thus very little gap 309 exists between the blunt 201 and the shaft 303 along at least a first circumferential portion of the inner diameter of the shaft 303. However, fluid flow is allowed to occur through the opening 305 which exists above the solid blunt 201 as shown in FIG. 3A. The blunt 201 includes material at or above the centerline 207 as shown in FIG. 3A so that the blunt cannot move substantially in a perpendicular direction relative to the longitudinal movement of the blunt 201 within the shaft 303. That is, by having solid material of the blunt at or above the centerline of the shaft 303, the blunt resists movement in this perpendicular direction.

Figure 2B:
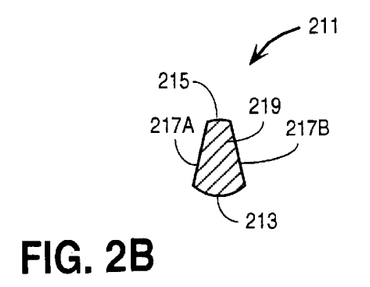
Figure 3B:
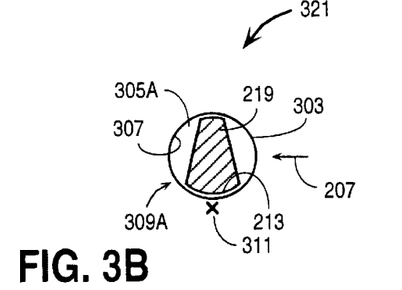

FIG. 2B shows another example of a particular geometry of a solid blunt according to the present invention. This particular geometry is referred to as a pie-slice shaped solid blunt due to the fact that the cross-section of the blunt as shown in FIG. 2B resembles a pie slice. The blunt 211 of FIG. 2B includes a first circumferential portion or outer surface 213 and a second circumferential portion or outer surface 215. Each of these circumferential portions are designed to come in close contact with the inner diameter of the shaft 303 as shown in FIG. 3B. In one case, the outer diameter of the blunt is nearly equal to (but just less than) the inner diameter of shaft 303. Thus, only a very small gap exists between the portion 213 and the inner diameter 307 of the shaft 303 as shown in FIG. 3B. The solid interior 219 of the blunt 211 extends from one circumferential portion to the other circumferential portion, thereby resisting perpendicular movement of the blunt. FIG. 2B shows in its cross-sectional view a particular geometry in which the sides 217a and 217b are straight. It will be appreciated that alternatively the sides 217a and 217b may be either concave or convex.

Figure 2C:
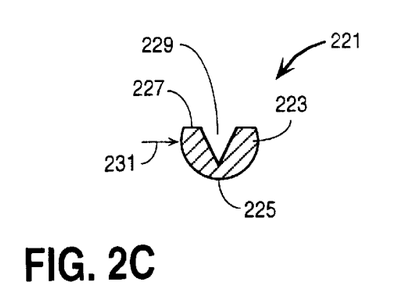
Figure 3C:
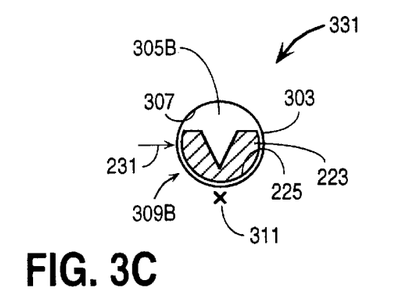

FIG. 2C shows another specific geometry of a solid blunt according to the present invention. The solid blunt 221 shown in the cross-sectional view of FIG. 2C includes a cut-out region 229. Even with the cut-out region, a solid portion 223 of the blunt 221 extends beyond the centerline 231 of the shaft 303 as shown in FIG. 3C. Accordingly, the solid blunt 221 will resist perpendicular movement as described above. The outer circumferential portion 225 of the solid blunt 221 has a diameter which is nearly equal to (but just less than) the diameter of the shaft 303 and thus very little space or gap 309 exists between the outer surface of the solid blunt and the inner diameter 307 of the shaft 303. Also as shown in FIG. 3C, the blunt is positioned relative to the sharp tip 311 so that a majority of the solid blunt material will be disposed next to the sharp tip 311.

Figure 2D:
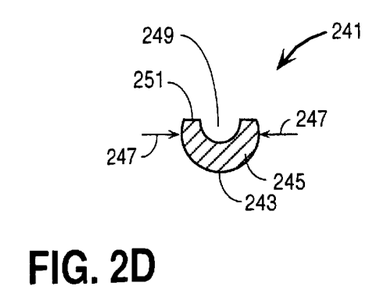
Figure 3D:
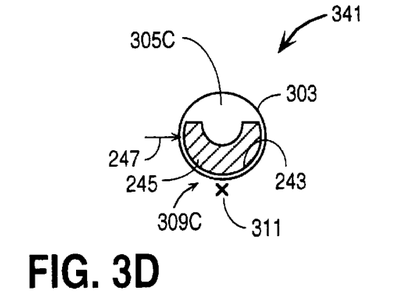

FIG. 2D shows another example of a particular geometry of a solid blunt according to the present invention. In the cross-sectional view of FIG. 2D, the blunt 241 includes a D-shaped cut-out 249 in the upper surface 251 of the blunt. Sufficient solid material 245 of the blunt is at or above the centerline 247 of the shaft 303 as shown in FIG. 3D. The outer circumferential portion 243 of the blunt 241 is sized relative to the inner diameter of the shaft 303 such that very little gap 309c exists between the inner diameter of the shaft 303 and the outer circumference of the blunt 241. The blunt 241 is positioned relative to the sharp tip 311 so that most of its solid material will be positioned near the tip 311.

Figure 3E:
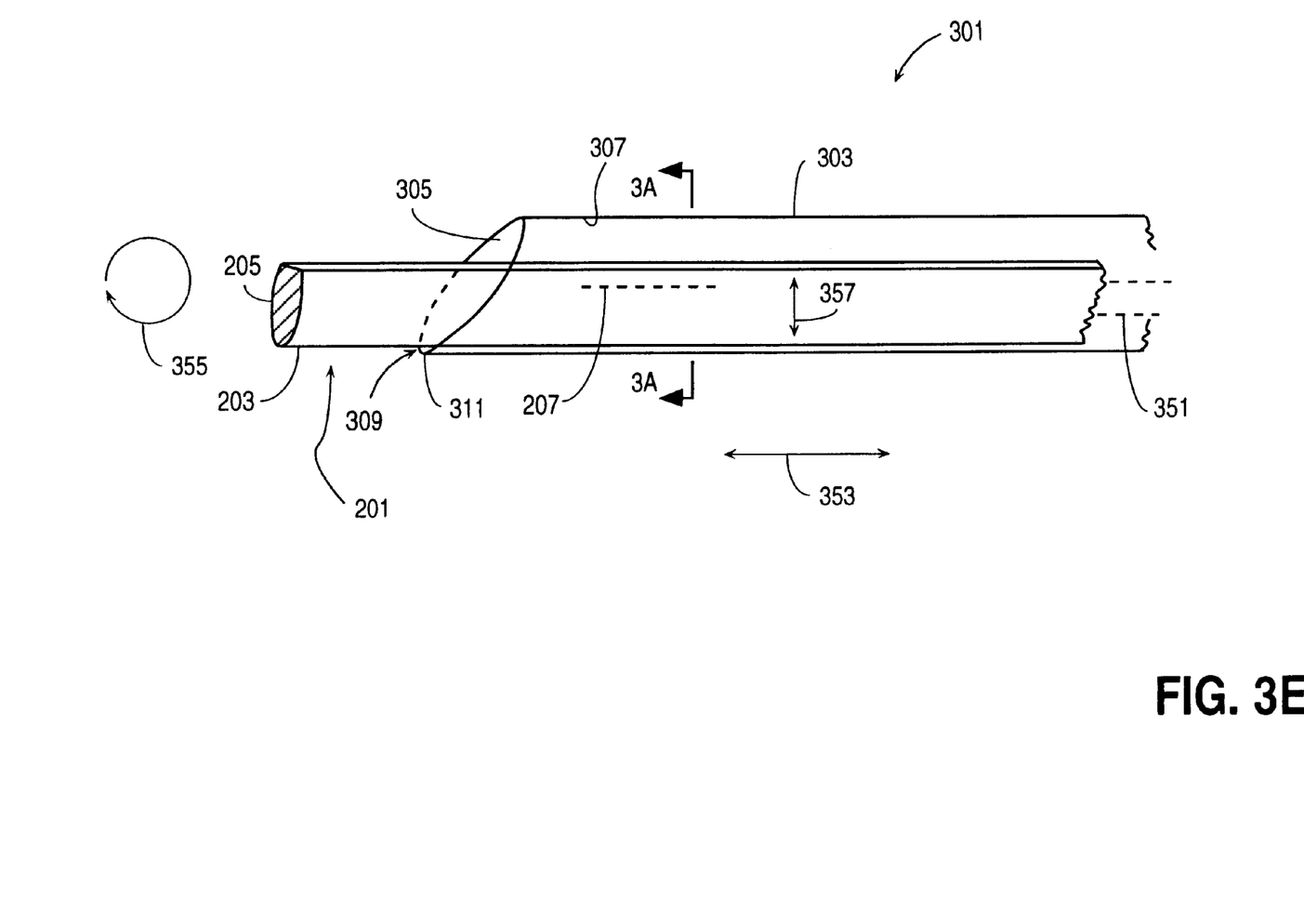
FIG. 3E shows the perspective side view of a needle and blunt assembly according to the present invention.

FIG. 3E shows a side perspective view of the assembly 301 shown in FIG. 3A. The cross-sectional view of FIG. 3A is shown by line 3A—3A of FIG. 3E. The needle assembly 301, as shown in FIG. 3E, includes the solid blunt 201 which is disposed within the hollow inner diameter of the cannula formed by the shaft 303. The inner diameter 307 of the shaft 303 is nearly equal to (but just less than) the outer diameter of the blunt 201 such that the gap 309 is very small. The gap 305 between the top of the solid blunt 201 and the inner diameter 307 provides a sufficient fluid path through the shaft 303 when the needle is used. On the other hand, the close proximity between the outer circumferential portion 203 of the blunt 201 and its corresponding inner circumferential portion of the shaft 303 is such that fluid flow through the gap 309 is relatively restricted. The centerline 207 of the shaft 303 is shown relative to the solid blunt 201. It can be seen that a portion of the solid material of the solid blunt is at or above the centerline, thereby preventing the blunt from moving perpendicularly along the perpendicular direction 357 shown in FIG. 3E. The blunt is capable of moving longitudinally along the longitudinal axis 353 under control of a conventional clip or other device (not shown) which is coupled to the blunt 201. This device, such as a clip, may be attached directly to the blunt or through an intermediary piece which may have a different profile such as the rod 351 shown in FIG. 3E. The rod 351 does not need to perform the functions of the solid blunt 201 and thus may have a different geometry than the solid blunt 201. The required geometry of the solid blunt 201 should exist around portions of the blunt that will be near the sharp tip 311. The clip or other device which controls and positions the solid blunt 201 may be similar to those devices in the prior art, such as those shown in U.S. Pat. Nos. 5,009,642, or 5,540,662, or 4,828,547, or 5,743,882. These clips or devices, using conventional mechanisms, allow for the blunt to move longitudinally but prevent the blunt from moving circularly (e.g. rotating) within the shaft 303; this circular direction is shown by the arrow 355 shown in FIG. 3E. Thus by using a conventional clip or other device for retaining and controlling the movement longitudinally of the blunt 201, the blunt 201 may be prevented from rotating (and thus stay positioned properly relative to the sharp tip 311) while also allowing for longitudinal movement along the axis 353 as shown in FIG. 3E. The geometric configuration of the blunt according to the present invention will also prevent perpendicular movement along the axis 357 as shown in FIG. 3E.

Figure 4A:
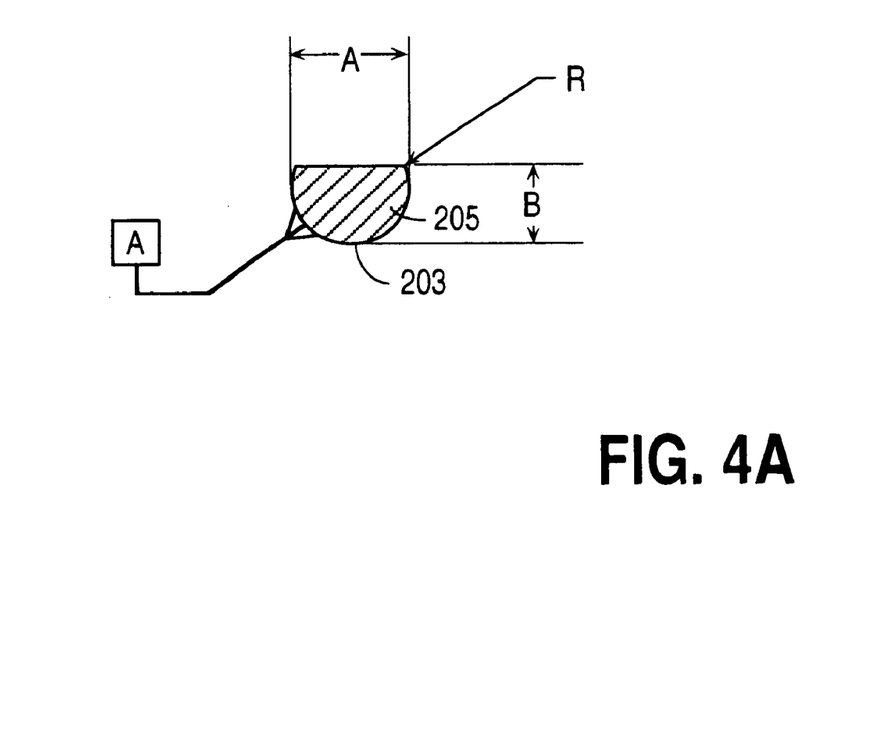
FIG. 4A shows another cross-sectional view of an example of a specific solid blunt according to the present invention.
Figure 4B:
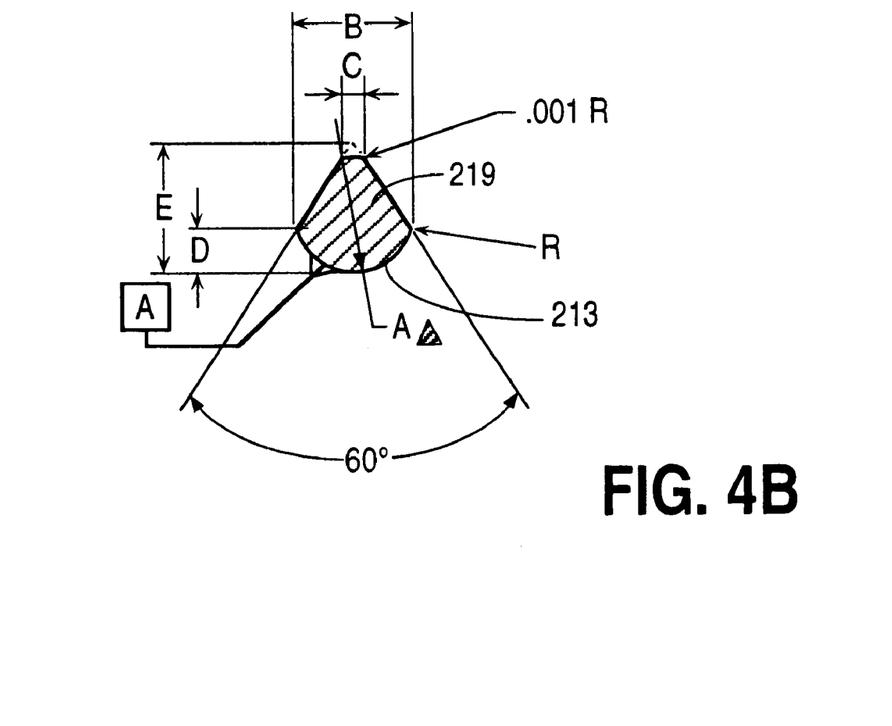
FIG. 4B shows another example of a specific solid blunt according to the present invention.

FIGS. 4A and 4B show respectively particular examples of the D-shaped solid blunt and the pie-slice shaped solid blunt according to the present invention. These particular figures and the following tables provide various specific examples for dimensions which are specified in the following tables. In particular, Table A below specifies examples for particular dimensions of the D-shaped blunt relative to certain specific needle shafts. Similarly, Table B shows examples of specific dimensions for the pie-slice shaped blunt of FIG. 4B. The tables show the nominal inner diameter (ID) of the needle and show the nominal outer diameter (OD) of the blunt. It can be seen that the OD of the blunt is less than but nearly equal to the ID of the needle. In a typical case, the OD of the blunt is 0.002 inches less than the ID of the blunt. The labels on the FIGS. 4A and 4B represent the same labeled dimensions in the Tables A and B (for example, "A" in FIG. 4A is a dimension shown in the column A ["Nominal Blunt OD"] of Table A). These examples of FIGS. 4A and 4B assume a cylindrical shape for the needle's shaft and the blunt so that a diameter may be used to describe the relative dimensions. It will be appreciated that other geometries for the needle and blunt may be used with the present invention; for example, a needle and a blunt each having triangular or elliptical cross-sections may be used where a dimension of the blunt nearly equals a dimension of the needle.

TABLE A

| Nominal Needle ID | Nominal Blunt OD A | B Flat Location |
|---|---|---|
| 0.050 | .0475 | .029 |
| 0.038 | .036 | .021 |
| 0.030 | .028 | .018 |
| 0.023 | .021 | .012 |
| 0.017 | .015 | .009 |
| 0.014 | .012 | .007 |

TABLE B

| Nominal Needle ID | Nominal Blunt OD A | B Base | C | D (Ref) | E (Ref) |
|---|---|---|---|---|---|
| 0.050 | .0475 | 0.0450 | 0.0122 | 0.0172 | 0.0573 |
| 0.038 | .036 | 0.0319 | 0.0048 | 0.0110 | 0.0400 |
| 0.030 | .028 | 0.0237 | 0.0024 | 0.0082 | 0.0300 |
| 0.023 | .021 | 0.0181 | 0.0018 | 0.0060 | 0.0225 |
| 0.017 | .015 | 0.0132 | 0.0018 | 0.0045 | 0.0165 |
| 0.014 | .012 | 0.0103 | 0.0012 | 0.0035 | 0.0130 |

Figure 5A:
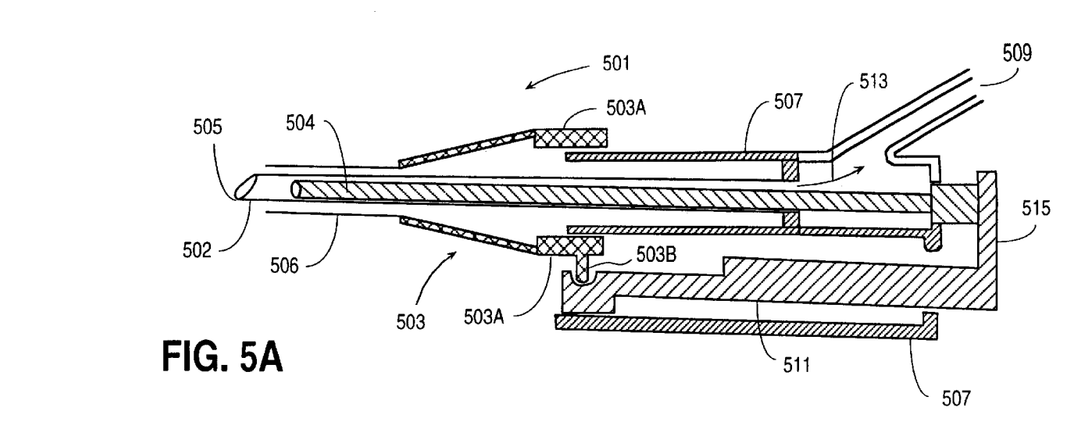
FIGS. 5A and 5B show cross-sectional views of an example of a catheter assembly which may use a solid blunt according to the present invention.
Figure 5B:
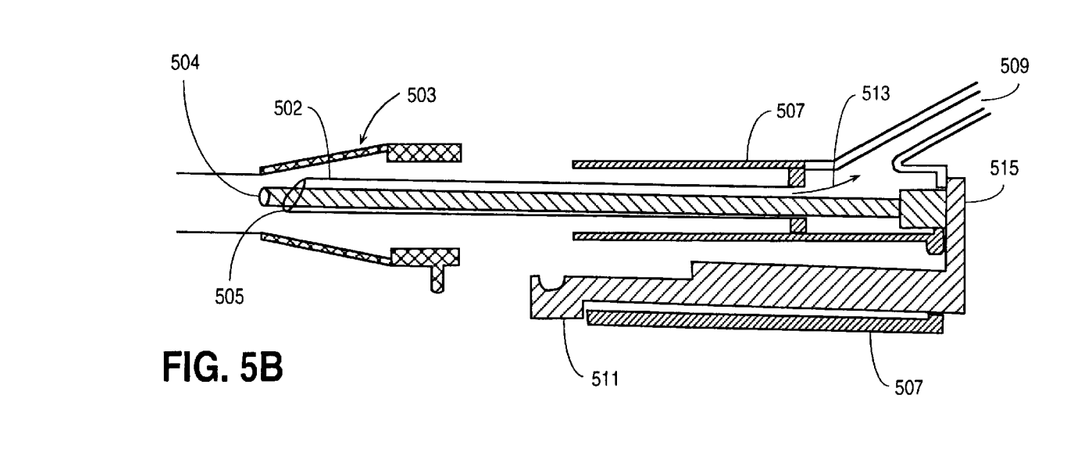

FIGS. 5A and 5B show an example of a catheter system 501 of the invention. It will be appreciated that the solid blunt of the present invention may be used with various different types of catheter systems and that FIGS. 5A and 5B show merely one example of such a system. The catheter system 501 includes a needle 502, a catheter hub 503, a solid D-shaped blunt 504, and a needle frame 507. The catheter hub 503 includes a tube 506 which surrounds the needle 502. The catheter hub 503 also includes a hub interconnect portion 503a which includes a section 503b disposed to engage a notch on the clip 511. FIG. 5A shows the catheter system set before the needle is used so that the blunt is within the shaft of the needle. The solid blunt 504 is disposed within the shaft of the needle 502 and will extend beyond the opening of the needle 502 and beyond the sharp tip 505 of the needle 502 after the needle is used in accordance with conventional operating mechanisms for moving blunts. FIG. 5B shows the catheter system after the needle is used. The needle frame 507 is coupled to a flash chamber 509 and is also coupled by means of a slidable joint to the end 515 of the blunt 504. The end 515 is coupled to the clip 511 so that when the catheter hub 503 is pulled away from the needle frame 507, the blunt 504 is pulled out (so that it extends out beyond the sharp tip 505) by the interaction between the hub at 503a and the clip at 511 and the lower portion of the needle frame 507. This lower portion of the needle frame 507 engages a portion of the clip 511 as shown in FIG. 5B after the catheter hub 503 has been pulled away from the needle frame 507. This engagement between the lower portion of the needle frame 507 and the clip will keep the blunt extended out beyond the sharp tip 505 as shown in FIG. 5B. Blood or other fluids which enter the opening of the needle 502 travel along the top of the solid blunt 504 along the line 513towards the flash chamber 509. It will be appreciated that the solid blunts of the present invention may be used with various different needle assemblies having various different types of clips and other mechanisms for positioning the solid blunt and for allowing for longitudinal movement of the solid blunt relative to the shaft of the needle.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A needle assembly comprising:

a cannula having an inner wall which defines an inner dimension and a sharp tip;

a solid blunt disposed within said cannula, the solid blunt having an outer dimension which is nearly equal to the inner dimension of the cannula, wherein solid blunt has at least a first position and a second position, the first position has the solid blunt disposed entirely within a cannula of a needle, and the second position has the solid blunt advanced sufficiently to extend a tip of the blunt beyond an opening in the cannula and the solid blunt substantially blocks fluid flow in a first space defined by a circumferential portion of the inner wall and allows fluid flow in a second space defined by the circumferential portion of the inner wall in either position.

2. A needle assembly as in claim 1, wherein the cannula has a substantially circular cross-section and the inner dimension is an inner diameter, and wherein the outer dimension is an outer diameter, wherein the solid blunt has a portion of a substantially circular cross-section, and wherein a first portion of the solid blunt having the outer dimension is configured be positioned near the sharp tip.

3. A needle assembly as in claim 2, wherein the solid blunt has one of: (a) a substantially D-shaped cross-section; (b) a substantial pie-slice shaped cross-section; and (c) a circular cross-section having a cut-out region wherein a second portion of the solid blunt extends from substantially near the first circumferential portion to at least a centerline of the cannula.

4. A needle assembly as in claim 3, wherein the cut-out region represents one of a "U" shape and a "V" shape.

5. A needle assembly as in claim 2, wherein the solid blunt is capable of longitudinal movement through the cannula and is prevented from moving substantially in a direction perpendicular to said longitudinal movement.

6. A needle assembly as in claim 5, wherein the longitudinal movement comprises movement between (a) a first position in which the solid blunt does not extend beyond the sharp tip and is within the cannula, and (b) a second position in which the solid blunt extends beyond the sharp tip and outside of the cannula.

7. A needle assembly as in claim 6, wherein the solid blunt is prevented from rotating in the cannula.

8. A needle assembly as in claim 6, wherein a portion of the solid blunt extends from substantially near the first circumferential portion to at least a centerline of the cannula.

9. A needle assembly as in claim 8, wherein the solid blunt least one-half of the inner diameter.

* * * * *

UNITED STATES PATENT AND TRADEMARK OFFICE
CERTIFICATE OF CORRECTION

PATENT NO. : 6,676,636 B2
DATED : January 13, 2004
INVENTOR(S) : Joseph Jawshin Chang et al.

It is certified that error appears in the above-identified patent and that said Letters Patent is hereby corrected as shown below:

Column 4,
Line 26, "circumferential portions are designed" should read -- circumferential portions is designed --

Column 6,
Line 62, "line 513towards the" should read -- line 513 towards the --

Column 7,
Line 15, "wherein solid blunt" should read -- wherein the solid blunt --

Column 8,
Line 2, "configured be positioned" should read -- configured to be positioned --
Line 5, "substantial" should read -- substantially --
Line 28, "solid blunt least one-half" should read
-- solid blunt extends at least one-half --

Signed and Sealed this

Sixteenth Day of March, 2004

JON W. DUDAS
*Acting Director of the United States Patent and Trademark Office*